United States Patent
Komiya et al.

(10) Patent No.: US 8,858,731 B2
(45) Date of Patent: Oct. 14, 2014

(54) CHEMICAL BOTTLE FOR ENDOSCOPE CLEANING/DISINFECTING APPARATUS AND ENDOSCOPE CLEANING/DISINFECTING APPARATUS

(71) Applicant: Olympus Medical System Corp., Tokyo (JP)

(72) Inventors: Takaaki Komiya, Hachioji (JP); Tsuyoshi Fujita, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/736,338

(22) Filed: Jan. 8, 2013

(65) Prior Publication Data

US 2013/0118537 A1 May 16, 2013

Related U.S. Application Data

(63) Continuation of application No. PCT/JP2012/060379, filed on Apr. 17, 2012.

(30) Foreign Application Priority Data

Jul. 8, 2011 (JP) .................................. 2011-152174

(51) Int. Cl.
*B08B 9/00* (2006.01)
*B65D 23/00* (2006.01)
*A61B 1/12* (2006.01)
*A61L 2/18* (2006.01)

(52) U.S. Cl.
CPC ................ *A61L 2/18* (2013.01); *A61L 2202/24* (2013.01); *B65D 23/00* (2013.01); *A61B 1/121* (2013.01)
USPC ........... 134/166 C; 134/113; 134/61; 134/84; 134/92; 134/94.1; 606/46; 422/292; 422/114

(58) Field of Classification Search
CPC ...... A61L 2202/24; A61L 2/18; A61B 18/14; A61B 18/1482; A61B 18/1492
USPC ............. 134/50, 56 R, 58 R, 61, 84, 92, 94.1, 134/95.1, 99.1, 113, 166 C; 422/3, 28, 114, 422/292; 215/379, 382; 606/46
See application file for complete search history.

(56) References Cited

U.S. PATENT DOCUMENTS 5,222,185 A * 6/1993 McCord, Jr. .................. 392/314
6,656,438 B1 12/2003 Kinoshita et al.
(Continued)

FOREIGN PATENT DOCUMENTS

DE        32 14 148 A1    12/1982
DE       101 63 635 C1    10/2003
(Continued)

OTHER PUBLICATIONS

Extended Supplementary European Search Report dated Nov. 22, 2013 from related European Application No. EP 12 81 1785.0.

*Primary Examiner* — Michael Barr
*Assistant Examiner* — Thomas Bucci
(74) *Attorney, Agent, or Firm* — Scully, Scott, Murphy & Presser, PC (57) ABSTRACT

A disinfecting chemical bottle includes a bottle body including a storing section that stores a chemical used for cleaning/disinfecting an endoscope and a mouth portion including an opening portion from which the chemical freely flows out, a first conductive portion provided so as to be exposed in an inner portion and an outer portion of the bottle body, and a second conductive portion provided at a position different from that of the first conductive portion so as to be exposed in the inner portion and the outer portion of the bottle body, the second conductive portion being electrically connectable to the first conductive portion via the chemical in the bottle body.

4 Claims, 4 Drawing Sheets

(56) References Cited

U.S. PATENT DOCUMENTS

2008/0115814 A1     5/2008  Hasegawa et al.
2008/0267812 A1*   10/2008  Kawachi et al. ................... 422/3

FOREIGN PATENT DOCUMENTS

| | | | | |
|---|---|---|---|---|
| EP | 1 025 862 A2 | * | 8/2000 | ................ A61L 2/26 |
| EP | 1 025 862 | * | 9/2000 | ................ A61L 2/26 |
| EP | 1 985 315 A1 | | 10/2008 | |
| JP | 2000-288069 | | 10/2000 | |
| JP | 2003-111725 | | 4/2003 | |
| JP | 2006-230493 | | 9/2006 | |
| JP | 2008-272114 | | 11/2008 | |
| JP | 2009-112343 | | 5/2009 | |
| JP | 2009-261683 | | 11/2009 | |
| WO | 02/27280 A2 | | 4/2002 | |

* cited by examiner

CHEMICAL BOTTLE FOR ENDOSCOPE CLEANING/DISINFECTING APPARATUS AND ENDOSCOPE CLEANING/DISINFECTING APPARATUS

CROSS REFERENCE TO RELATED APPLICATION

This application is a continuation application of PCT/JP2012/060379 filed on Apr. 17, 2012 and claims benefit of Japanese Application No. 2011-152174 filed in Japan on Jul. 8, 2011, the entire contents of which are incorporated herein by this reference.

BACKGROUND OF THE INVENTION

1. Field of the Invention

The present invention relates in particular to a chemical bottle for an endoscope cleaning/disinfecting apparatus, which is provided for a chemical for cleaning/disinfecting an endoscope, and an endoscope cleaning/disinfecting apparatus.

2. Description of the Related Art

Conventionally, endoscopes used in a medical field are cleaned and disinfected using an endoscope cleaning/disinfecting apparatus each time endoscopy is done. A disinfecting liquid for disinfection is generally prepared by pouring a concentrated disinfecting chemical charged in advance in a chemical bottle into a diluting tank and diluting the concentrated disinfecting chemical with diluting liquid such as water. In this case, if the diluting liquid is supplied after the concentrated disinfecting chemical is poured into the diluting tank, the diluting tank may deteriorate. Therefore, for example, Japanese Patent Application Laid-Open Publication No. 2009-261683 discloses a technique for preparing a disinfecting liquid by, upon detection of supply of a predetermined amount of diluting liquid to a diluting tank by a sensor disposed on a wall surface of the diluting tank, stopping the supply of the diluting liquid and supplying a concentrated disinfecting liquid from a chemical bottle, and when supply of a predetermined amount of the concentrated disinfecting liquid is detected by the sensor, stopping the supply of the concentrated disinfecting liquid.

SUMMARY OF THE INVENTION

A chemical bottle for an endoscope cleaning/disinfecting apparatus according to an aspect of the present invention includes: a bottle body that is detachable from the endoscope cleaning/disinfecting apparatus, and includes a storing section that stores a chemical used for cleaning/disinfecting an endoscope and a mouth portion including an opening portion from which the chemical freely flows out; a film portion provided between the storing section and the mouth portion, the film sealing the bottle body; a first conductive portion disposed on the storing section side via the film portion and provided so as to be exposed from an inner portion to an outer portion of the bottle body; and a second conductive portion disposed on the mouth portion side via the film portion and provided so as to be exposed in the inner portion and the outer portion of the bottle body, the second conductive portion being electrically connectable to the first conductive portion via the chemical in the bottle body.

Also, an endoscope cleaning/disinfecting apparatus according to an aspect of the present invention includes: the above-stated chemical bottle for an endoscope cleaning/disinfecting apparatus; a bottle disposition portion in which the chemical bottle for an endoscope cleaning/disinfecting apparatus is disposed; a first contact terminal positioned so as to be in contact with the first conductive portion of the chemical bottle for an endoscope cleaning/disinfecting apparatus disposed at the bottle disposition portion; a second contact terminal positioned so as to be in contact with the second conductive portion of the chemical bottle for an endoscope cleaning/disinfecting apparatus disposed at the bottle disposition portion; an electrical connection recognition section capable of recognizing electrical connection between the first contact terminal and the second contact terminal by connecting the electrical connection recognition section to the first contact terminal and the second contact terminal; and an endoscope cleaning/disinfecting section connected to the bottle disposition portion.

DETAILED DESCRIPTION OF THE PREFERRED EMBODIMENT

Hereinafter, an embodiment of the present invention will be described with reference to the drawings.

Figure 1:
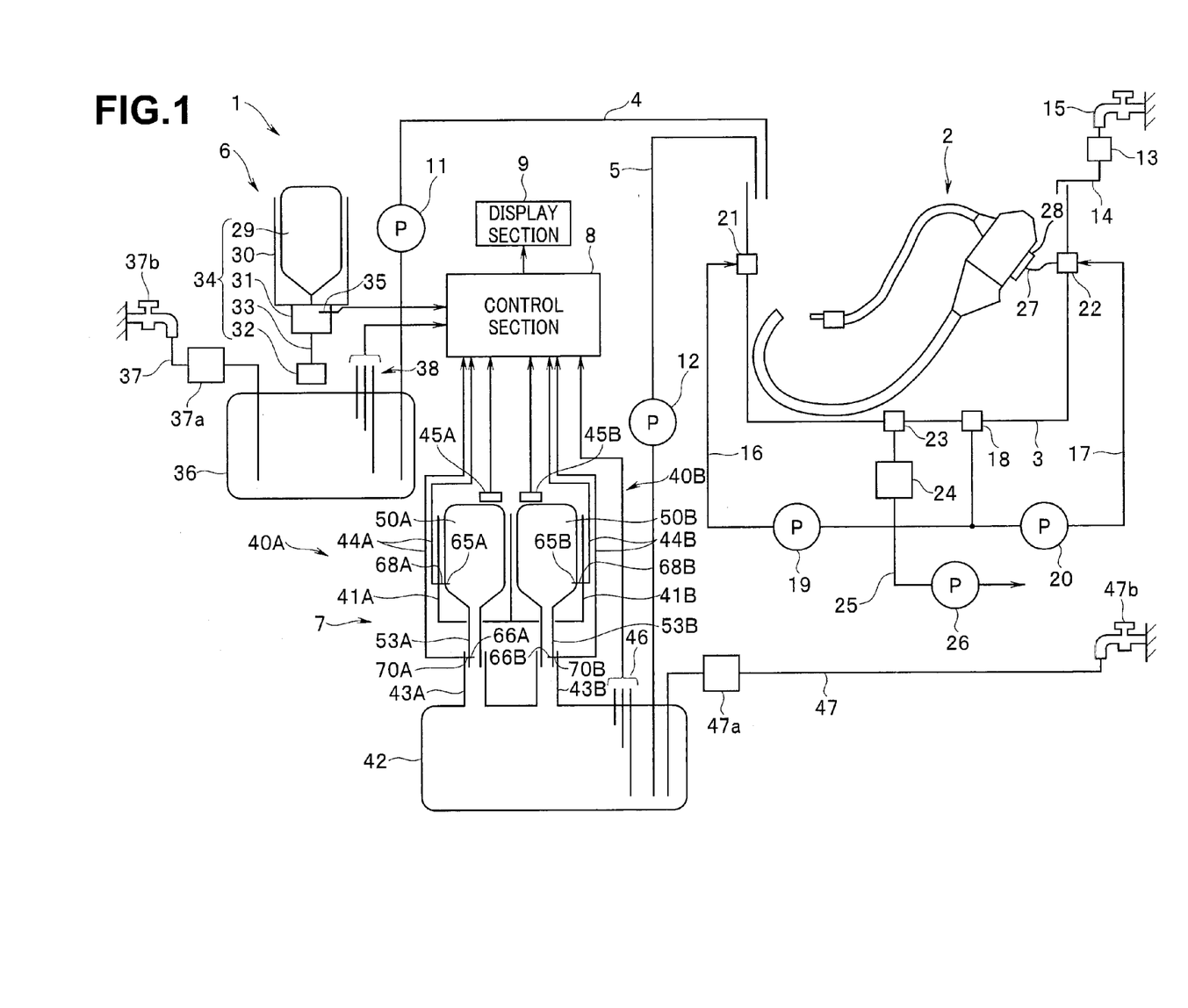
FIG. 1 is a diagram of a schematic overall configuration of an endoscope cleaning/disinfecting apparatus.

In FIG. 1, reference numeral 1 denotes an endoscope cleaning/disinfecting apparatus, and the endoscope cleaning/disinfecting apparatus 1 mainly includes a cleaning/disinfecting bath 3 as an endoscope cleaning/disinfecting section that holds and cleans/disinfects an endoscope 2 or non-illustrated endoscope accessories, which are objects to be cleaned/disinfected, a cleaning chemical diluting mechanism 6 and a disinfecting chemical diluting mechanism 7 connected to the cleaning/disinfecting bath 3 via a cleaning liquid supply conduit 4 and a disinfecting liquid supply conduit 5, respectively, a control section 8 that controls the cleaning chemical diluting mechanism 6 and the disinfecting chemical diluting mechanism 7, and a display section 9 that provides information such as a control result by means of displaying.

Pumps 11 and 12 are inserted partway through the cleaning liquid supply conduit 4 and the disinfecting liquid supply conduit 5, respectively, and a cleaning liquid and a disinfecting liquid prepared in the cleaning chemical diluting mechanism 6 and the disinfecting chemical diluting mechanism 7, respectively, under the control of the control section 8 are, for example, pumped and supplied into the cleaning/disinfecting bath 3.

The cleaning/disinfecting bath 3 is connected to a water supply source such as a faucet 15 via a water deliver conduit 14 equipped with a water supply valve 13, and also to an (endoscope) outer surface cleaning/disinfecting conduit 16 and an (endoscope) conduit inner surface cleaning/disinfecting conduit 17.

One end of the outer surface cleaning/disinfecting conduit 16 and one end of the conduit inner surface cleaning/disinfecting conduit 17 are joined to a circulating water discharge port 18 at a bottom part of the cleaning/disinfecting bath 3, and the other ends are connected to, for example, liquid supply ports 21 and 22 provided at respective wall surfaces of the cleaning/disinfecting bath 3 via pumps 19 and 20 inserted partway, respectively.

Also, a liquid discharge port 23 provided at the bottom surface of the cleaning/disinfecting bath 3 is connected to a liquid discharge conduit 25 equipped with a liquid discharge valve 24, and a pump 26 that performs liquid discharge is connected to a position partway through the liquid discharge conduit 25.

Note that the liquid supply port 22 is connected to a connection portion 28 of a fluid pipe sleeve that performs, e.g., air/water supplying, which is provided at the endoscope 2 via a connection tube 27 inside the cleaning/disinfecting bath 3.

The pumps 11, 12, 19, 20 and 26, the water supply valve 13 and the liquid discharge valve 24, which are described above, are controlled by the control section 8. Furthermore, an electromagnetic valve and the like, which are described later, are also controlled by the control section 8.

On the other hand, the cleaning chemical diluting mechanism 6 includes a gravity-feed cleaning chemical supply section 34 including a cleaning chemical bottle (also simply referred as chemical bottle) 29 charged with a concentrated cleaning chemical and a bottle holding portion 30, a cleaning chemical reservoir tank (also simply referred as reservoir tank) 31 as a storage tank that is connected to the chemical bottle 29 via the bottle holding portion 30 and stores a predetermined amount of cleaning chemical, and a (cleaning) chemical supply conduit 33 that is connected to the reservoir tank 31 and equipped with an electromagnetic valve 32 as an opening/closing portion that opens/closes in the vicinity of an lower end thereof.

The lower end of the chemical supply conduit 33 of the cleaning chemical supply section 34 is connected to a cleaning chemical diluting tank (also referred to simply as diluting tank) 36, and when the electromagnetic valve 32, which is controlled by the control section 8 to open/close, is opened, a cleaning chemical from the reservoir tank 31 is supplied into the diluting tank 36 by its own weight. Note that in the reservoir tank 31, a water level sensor 35, which is a water-level detecting sensor that detects a water level of a cleaning chemical inside the reservoir tank 31, is provided, and a detection signal from the water level sensor 35 is inputted to the control section 8.

Also, the diluting tank 36 is connected to one end side of a dilution conduit 37 with a diluting valve 37a provided partway therethrough and the other end is connected to, for example, a faucet 37b, which is a water supply source of diluting water.

Furthermore, the diluting tank 36 is provided with a water level sensor 38 that detects amounts of diluting water and cleaning chemical supplied into the diluting tank 36, and detection signals from the water level sensor 38 are inputted to the control section 8.

When an amount of cleaning chemical for performing one (endoscope) cleaning is blended with and thus diluted with diluting water and stored as a cleaning liquid in the diluting tank 36 and a cleaning step of performing cleaning is started under the control of the control section 8, the control section 8 drives the pump 11 to supply the cleaning liquid into the cleaning/disinfecting bath 3.

Since in the present embodiment, two types of disinfecting chemicals, a first disinfecting chemical and a second disinfecting chemical (for example, the first disinfecting chemical is a disinfecting chemical main agent and the second disinfecting chemical is a disinfecting chemical activating agent for activation) are used, the disinfecting chemical diluting mechanism 7 mainly includes two gravity-feed disinfecting chemical supply sections 40A and 40B.

The disinfecting chemical supply section 40A includes a disinfecting chemical bottle (also simply referred to as chemical bottle) 50A with a concentrated first disinfecting chemical charged in advance, a bottle disposition portion 41A in which the chemical bottle 50A is disposed and held so as to be inclined in a predetermined manner as described below, a bottle attachment portion 43A that is connected to a lower end side of a mouth portion 53A of the chemical bottle 50A and provided at an upper surface of a disinfecting chemical diluting tank (also simply referred to as diluting tank) 42 to which the chemical bottle 50A is detachably connected in an inclined state, a chemical detection section 44A that is connected to the control section 8 and detects a chemical in the chemical bottle 50A, and a bottle detecting section 45A that is connected to the control section 8 and detects disposition of the chemical bottle 50A in the bottle disposition portion 41A.

The disinfecting chemical supply section 40B is configured similarly to the disinfecting chemical supply section 40A and includes a disinfecting chemical bottle (also simply referred to as chemical bottle) 50B with a concentrated second disinfecting chemical charged in advance, a bottle disposition portion 41B in which the chemical bottle 50B is disposed and held so as to be inclined in a predetermined manner as described below, a bottle attachment portion 43B that is connected to a lower end side of a mouth portion 53B of the chemical bottle 50B and provided at an upper surface of a diluting tank 42 to which the chemical bottle 50B is detachably connected in an inclined state, a chemical detection section 44B that is connected to the control section 8 and detects a chemical in the chemical bottle 50B, and a bottle detecting section 45B that is connected to the control section 8 and detects disposition of the chemical bottle 50B in the bottle disposition portion 41B.

In the diluting tank 42, a water level sensor 46 that detects an initial water level of a diluting water supplied in the diluting tank 42, a water level of disinfecting water obtained by diluting the first disinfecting chemical and the second disinfecting chemical with diluting water, and an abnormal water level, and detection signals from the water level sensor 46 are inputted to the control section 8.

Also, the diluting tank 42 is connected to one end side of a diluting conduit 47 with a diluting valve 47a provided partway therethrough, and the other end is connected to, for example, a faucet 47b that serves as a water supply source of the diluting water.

In the present embodiment, for example, preparation of a disinfecting liquid as described below is performed under the control of the control section 8.

First, when the chemical bottles 50A and 50B are removed from the disinfecting chemical supply sections 40A and 40B, respectively, the diluting valve 47a is opened to supply diluting water to the diluting tank 42 with a preset water level (lowest water level to be detected) as an upper limit water level.

When it is detected that the chemical bottles 50A and 50B are newly attached to the bottle attachment portions 43A and 43B, respectively, after or before the upper limit water level is reached, the diluting valve 47a is opened again or continuously to supply the diluting water to the diluting tank 42 until a second highest water level is reached, whereby a disinfecting liquid having a proper concentration is prepared.

Subsequently, if the water level rises to a highest water level for any cause, such water level is determined as an abnormal water level, and the diluting valve 47a is closed to stop the supply of the diluting water.

Then, when a disinfecting chemical is blended with and thus, diluted with the diluting water and stored as a disinfecting liquid, and a disinfecting step is started, the control section 8 drives the pump 12 to supply the disinfecting liquid into the cleaning/disinfecting bath 3.

Figure 2A:
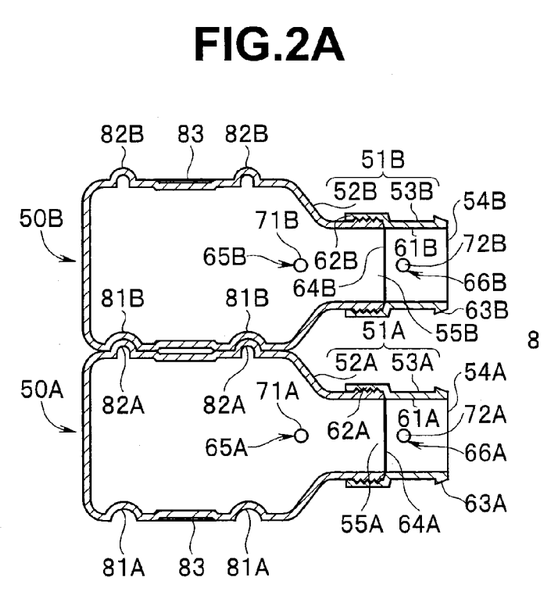
FIG. 2A is a cross-sectional diagram of chemical bottles for an endoscope cleaning/disinfecting apparatus, which are arranged adjacent to each other, as viewed from above.
Figure 2B:
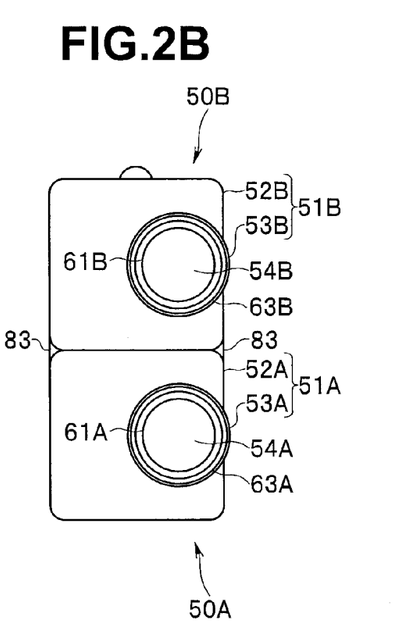
FIG. 2B is a side elevation of FIG. 2A as viewed from the mouth portion side.
Figure 2C:
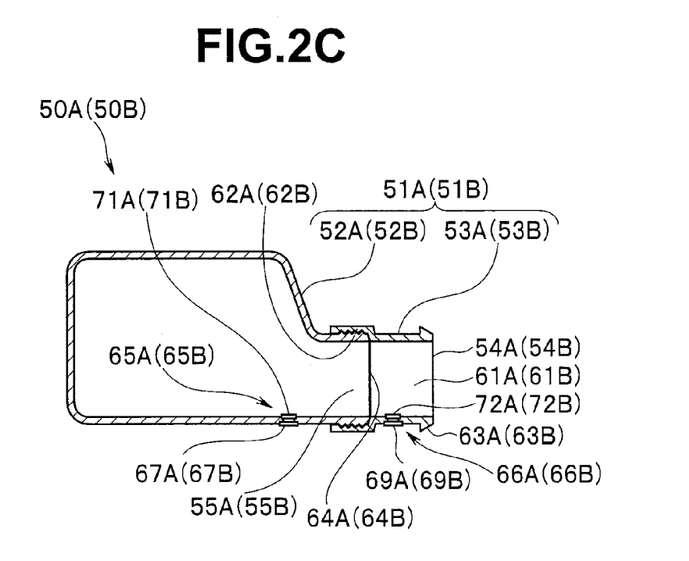
FIG. 2C is a cross sectional diagram of FIG. 2A as viewed from the front.

As illustrated in FIGS. 2A, 2B and 2C, the chemical bottles 50A and 50B are each formed in a shape of a bottle, bottle bodies 51 A and 51 B include storing sections 52A and 52B that each store a chemical, the mouth portions 53A and 53B including opening portions 54A and 54B from which the chemical freely flows out, respectively. The mouth portions 53A and 53B of the bottle bodies 51A and 51B are formed of ones each having a shape of a cap and extending outward from the opening portions 55A and 55B of the storing sections 52A and 52B, respectively.

Figure 3A:
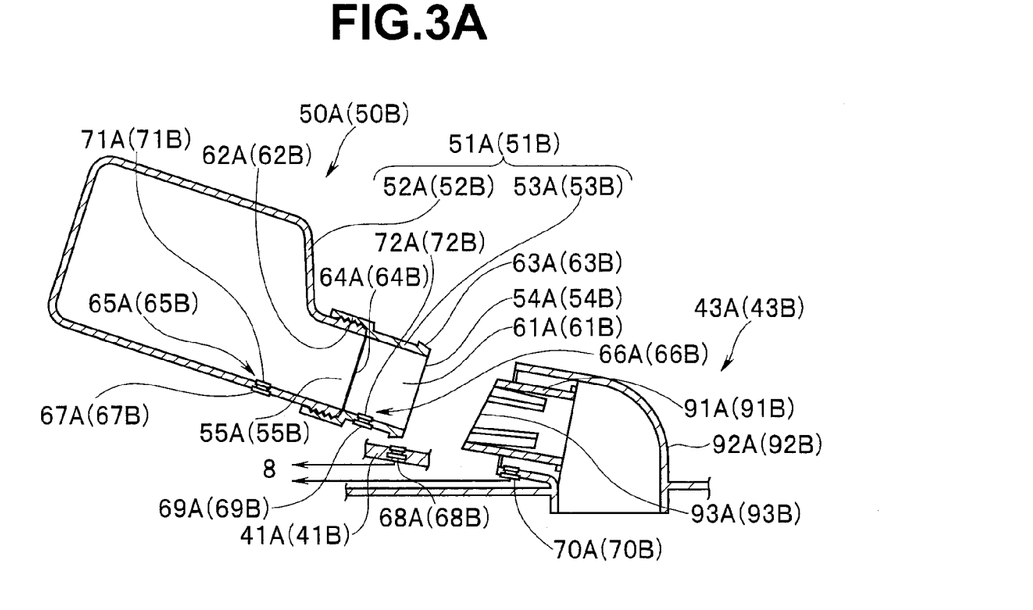
FIG. 3A is a diagram of a state before chemical bottles for an endoscope cleaning/disinfecting apparatus are attached to a bottle attachment portion.
Figure 3B:
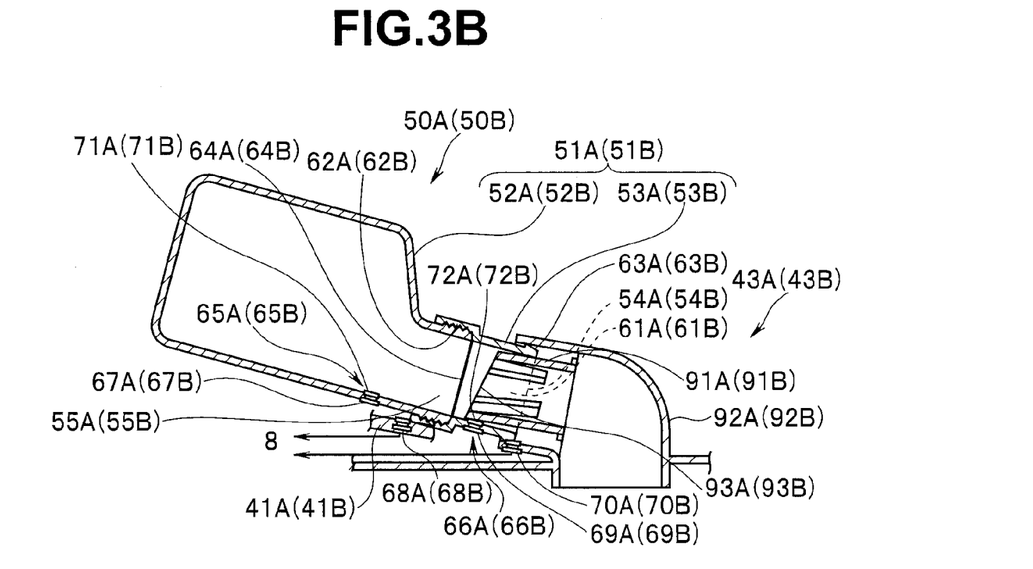
FIG. 3B is a diagram of a state while the chemical bottles for an endoscope cleaning/disinfecting apparatus being attached to the bottle attachment portion.
Figure 3C:
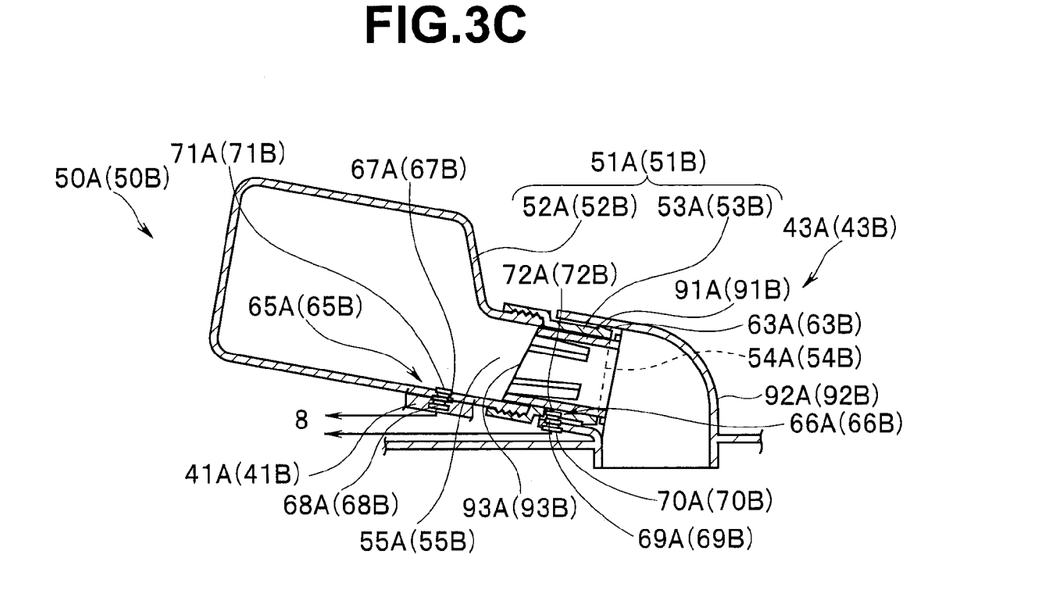
FIG. 3C is a diagram of a state in which the chemical bottles for an endoscope cleaning/disinfecting apparatus have been attached to the bottle attachment portion.

The mouth portions 53A and 53B of the chemical bottles 50A and 50B are provided at respective positions decentered relative to respective center axes of the storing sections 52A and 52B so that the liquids in the chemical bottles 50A and 50B are fully discharged by their own weight through the respective mouth portions 53A and 53B when the chemical bottles 50A and 50B are laid at a predetermined inclination (when the chemical bottles 50A and 50B are attached to the bottle attachment portions 43A and 43B of the disinfecting chemical supply sections 40A and 40B: see FIGS. 3A, 3B and 3C). More specifically, the mouth portions 53A and 53B are provided so that inner surfaces of one side wall of the storing sections 52A and 52B and inner surfaces of the mouth portions 53A and 53B are in a same plane (positioned within a same plane). Note that respective outflow surfaces when the respective chemicals flow out from the storing sections 52A and 52B from the opening portions 54A and 54B of the mouth portions 53A and 53B are referred to as bottom surfaces of the chemical bottles 50A and 50B, respectively.

The cap-shaped mouth portions 53A and 53B include cylindrical cap bodies 61A and 61B, attachment portions 62A and 62B that are formed at proximal ends of the cap bodies 61A and 61B and are attachable to the storing sections 52A and 52B of the bottle bodies 51A and 51B, and seal portions 63A and 63B including an elastic material, the seal portions 63A and 63B being formed at distal ends of the cap bodies 61 A and 61 B and projecting outward in respective radial directions of the mouth portions 53A and 53B. Then, the chemical bottles 50A and 50B are detachable from the bottle attachment portions 43A and 43B of the disinfecting chemical supply sections 40A and 40B via the cap-shaped mouth portions 53A and 53B, respectively.

Also, the mouth portions 53A and 53B include thin film portions 64A and 64B that are positioned at a boundary portion between the attachment portions 62A and 62B and the cap bodies 61A and 61B, and occlude the opening portions 55A and 55B of the storing sections 52A and 52B when the mouth portions 53A and 53B are attached to the storing sections 52A and 52B via the attachment portions 62A and 62B, respectively.

Furthermore, first conductive portions 65A and 65B exposed in inner portions and outer portions of the bottle bodies 51A and 51B are provided at bottom surfaces on the storing section 52A and 52B sides of the chemical bottles 50A and 50B, respectively. The first conductive portions 65A and 65B can be disposed at, for example, a center in a width direction.

Also, second conductive portions 66A and 66B that are electrically connectable to the first conductive portions 65A and 65B via the respective chemicals in the bottle bodies 51A and 51B on bottom surfaces on the cap body 61A and 61B sides of the mouth portions 53A and 53B of the chemical bottles 50A and 50B.

A material for the first conductive portions 65A and 65B is not specifically limited, and preferably includes, for example, a substance having an anticorrosive property and conductivity. More specifically, the material preferably includes, e.g., a stainless steel material. Outer exposed surfaces 67A and 67B, which are exposed in the outer portions of the bottle bodies 51A and 51B, can contact with first contact terminals 68A and 68B provided at the bottle disposition portions 41A and 41B of the disinfecting chemical supply sections 40A and 40B and connected to the control section 8, respectively.

Also, a material for the second conductive portions 66A and 66B is not specifically limited, and preferably includes for example, a substance having an anticorrosive property and conductivity. More specifically, the material preferably includes, e.g., a stainless steel material. Outer exposed surfaces 69A and 69B, which are exposed in the outer portions of the bottle bodies 51A and 51B, can contact with second contact terminals 70A and 70B provided at the bottle attachment portions 43A and 43B of the disinfecting chemical supply sections 40A and 40B and connected to the control section 8, respectively.

As described above, in the present embodiment, the control section 8 is provided as an electrical connection recognition section.

When the chemical bottles 50A and 50B are attached to the bottle disposition portions 41A and 41B and the bottle attachment portions 43A and 43B, respectively, electrical connection between the first conductive portions 65A and 65B and the second conductive portions 66A and 66B is recognized via the first contact terminals 68A. and 68B and the second contact terminals 70A. and 70B. At this time, inner exposed surfaces 71A and 71B of the first conductive portions 65A and 65B, which are exposed in the inner portions of the bottle bodies 51A and 51B, and inner exposed surfaces 72A and 72B of the second conductive portions 66A and 66B, which are exposed in the inner portions of the bottle bodies 51 A and 51 B, are connected via a conductive liquid, that is, the respective chemicals, whereby electrical connection between the first conductive portions 65A and 65B and the second conductive portions 66A and 66B are detected and the respective chemicals in the chemical bottles 50A and 50B flow out to the mouth portions 53A and 53B from the storing sections 52A and 52B.

On the other hand, if the first conductive portions 65A and 65B and the second conductive portions 66A and 66B are not electrically connected, no chemicals in the chemical bottles 50A and 50B flow out from the storing sections 52A and 52B to the mouth portions 53A and 53B, and in this case, there are the following two types of detection results.

In other words, if the first conductive portions 65A and 65B and the second conductive portions 66A and 66B are not electrically connected, respectively, after detection of installation of the chemical bottles 50A and 50B by the bottle detecting sections 45A and 45B, it is detected that the respective chemicals are contained in the chemical bottles 50A and 50B but do not yet flow out.

Also, if the first conductive portions 65A and 65B and the second conductive portions 66A and 66B are first electrically connected and then become electrically unconnected, respectively, it is detected that outflow of the respective chemicals in the chemical bottles 50A and 50B is substantially completed.

Furthermore, a pair of recess portions 81A and a pair of recess portions 81B are provided at respective side walls on one side adjacent to the bottom surfaces of the storing sections 52A and 52B of the chemical bottles 50A and 50B along respective longitudinal directions of the storing sections 52A and 52B. Furthermore, a pair of projection portions 82A and a pair of projection portions 82B are provided along the respective longitudinal directions of the storing sections 52A and 52B at respective side walls on the other side adjacent to the bottom surfaces of the storing sections 52A and 52B of the chemical bottles 50A and 50B.

As described above, in the present embodiment, in order to charge two types of chemicals (that is, the first disinfecting chemical and the second disinfecting chemical) into the diluting tank 42 simultaneously without fail, as illustrated in FIGS. 2A, 2B and 2C, the chemical bottle 50A and the chemical bottle 50B are integrally assembled without displacing in their respective longitudinal directions relative to each other by engaging the recess portions 81B of the chemical bottle 50B with the projection portions 82A of the chemical bottle 50A. Then, in such integrated state, as illustrated in FIG. 2B, the mouth portions 53A and 53B of the chemical bottles 50A and 50B are directed so as to be positioned side by side in a lateral direction. Also, such assembling state is firmly maintained by, e.g., a shrink film 83 winding the side walls of the two chemical bottles 50A and 50B in an integrated manner.

On the other hand, as illustrated in FIGS. 3A, 3B and 3C, the bottle attachment portions 43A and 43B, to which the chemical bottles 50A and 50B are detachably attached, include respective charge ports for charging a concentrated disinfecting chemical liquid into the diluting tank 42.

The bottle attachment portions 43A and 43B include bottle receiving portions 91A and 91B that receive the occluded opening portions 55A and 55B of the storing sections 52A and 52B of the chemical bottles 50A and 50B in an air-tight and liquid-tight manner (via the mouth portions 53A and 53B in the present embodiment), charge holes 92A and 92B that guide the respective chemicals into the diluting tank 42, and protrusion portions 93A and 93B that open the film portions 64A and 64B to make the storing sections 52A and 52B communicate with the diluting tank 42 through the charge holes 92A and 92B with the mouth portions 53A and 53B of the chemical bottles 50A and 50B received by the bottle receiving portions 91A and 91B in an air-tight and liquid-tight manner (the state in FIG. 3C), respectively.

The above-described bottle receiving portions 91A and 91B each have a double-tube structure including an outer tube and an inner tube concentrically disposed, and respective annular gaps between the outer tubes and the inner tubes are set to have dimensions substantially equal to respective thicknesses of the mouth portion 53A and 53B of the chemical bottles 50A and 50B, whereby the mouth portions 53A and 53B fit in the respective annular gaps between the outer tubes and the inner tubes in an air-tight and liquid-tight manner. Also, the protrusion portions 93A and 93B are provided inside the respective inner tubes in the charge holes 92A and 92B, and respective distal end surfaces of the protrusion portions 93A and 93B are inclined in a tapered manner and respective inner holes of the protrusion portions 93A and 93B are in communication with the charge holes 92A and 92B.

Here, FIGS. 3A, 3B and 3C are diagrams illustrating a procedure for attaching new chemical bottles 50A and 50B to the bottle attachment portions 43A and 43B, respectively, and first, in the state in FIG. 3A, new chemical bottles 50A and 50B are inclined so that toward the opening portions 54A and 54B of the mouth portions 53A and 53B of the chemical bottles 50A and 50B face the bottle receiving portions 91A and 91B of the bottle attachment portions 43A and 43B, respectively. At this time, the first contact terminals 68A and 68B of the bottle disposition portions 41A and 41B and the second contact terminals 70A and 70B of the bottle attachment portions 43A and 43B are not electrically connected, respectively.

Next, as illustrated in FIG. 3B, the mouth portions 53A and 53B of the new chemical bottles 50A and 50B are pushed to the back along the bottle receiving portions 91A and 91B of the bottle attachment portions 43A and 43B. At this time, when the protrusion portions 93A and 93B of the bottle attachment portions 43A and 43B do not reach the respective film portions 64A and 64B, the film portions 64A and 64B are not opened, and thus, respective chemicals remain in the respective storing sections 52A and 52B. Thus, the first contact terminals 68A and 68B and the second contact terminals 70A and 70B are not electrically connected.

Subsequently, when the mouth portions 53A and 53B of the new chemical bottles 50A and 50B are further pushed to the back along the bottle receiving portions 91A and 91B of the bottle attachment portions 43A and 43B, the protrusion portions 93A and 93B of the bottle attachment portions 43A and 43B reach the film portions 64A and 64B, and the film portions 64A and 64B are thereby opened, respectively. Consequently, the respective chemicals in the storing sections 52A and 52B start flowing out to the mouth portions 53A and 53B via respective opened parts of the film portions 64A and 64B and flow into the diluting tank 42 along the charge holes 92A and 92. At this stage, the first contact terminals 68A and 68B and the second contact terminals 70A and 70B are electrically connected via respective chemicals interposed between the inner exposed surfaces 71A and 71B of the first conductive portions 65A and 65B, which are exposed in the respective inner portions of the mouth portions 53A and 53B and the inner exposed surfaces 72A and 72B of the second conductive portions 66A and 66B, which are exposed in the respective inner portions of the bottle bodies 51A and 51B, whereby it is detected that the respective chemicals flow out from the storing sections 52A and 52B to the mouth portions 53A and 53B.

Then, as illustrated in FIG. 3C, when the respective chemicals flow out from the storing sections 52A and 52B to the mouth portions 53A and 53B with the mouth portions 53A and 53B of the chemical bottles 50A and 50B received by the bottle receiving portions 91A and 91B in an air-tight and liquid-tight manner, the electrical connection between the first contact terminals 68A and 68B and the second contact terminals 70A and 70B continues respectively.

Subsequently, when there are no remaining chemicals in the storing sections 52A and 52B, there are no chemicals between the inner exposed surfaces 71A and 71B of the first conductive portions 65A and 65B and the inner exposed surfaces 72A and 72B of the second conductive portions 66A and 66B, the electrical connection between the first contact terminals 68A and 68B and the second contact terminals 70A and 70B are discontinued, whereby it is detected that the respective chemicals in the chemical bottles 50A and 50B have substantially fully flowed out.

In the endoscope cleaning/disinfecting apparatus 1 configured as described above, first, in a cleaning step, the control section 8 activates the pump 11 to supply a cleaning liquid in the diluting tank 36 into the cleaning/disinfecting bath 3.

Subsequently, the control section 8 activates the pumps 19 and 20 to circulate the cleaning liquid in the cleaning/disinfecting bath 3, thereby cleaning the endoscope 2.

Upon end of the cleaning step, the control section 8 opens the liquid discharge valve 24 and activates the pump 26 to discharge the cleaning liquid from the cleaning/disinfecting bath 3.

Upon end of discharge of the cleaning liquid and end of a rinsing step of performing rinsing, the control section 8 starts a disinfecting step. In this case, the control section 8 activates the pump 12 to supply the disinfecting liquid in the diluting tank 42 into the cleaning/disinfecting bath 3. Subsequently, the control section 8 activates the pumps 19 and 20 to circulate the disinfecting liquid in the cleaning/disinfecting bath 3, thereby disinfecting the endoscope 2.

Upon end of the disinfecting step, the control section 8 opens the liquid discharge valve 24 and activates the pump 26 to discharge the disinfecting liquid from the cleaning/disinfecting bath 3.

Upon end of discharge of the disinfecting liquid, the control section 8 performs a rinsing step and ends the endoscope cleaning/disinfecting processing.

As described above, according to the embodiment of the present invention, the disinfecting chemical bottles 50A and 50B include: bottle bodies 51A and 51B including storing sections 52A and 52B that store respective chemicals used for cleaning/disinfecting the endoscope 2 and the mouth portions 53A and 53B including opening portions 54A and 54B from which the respective chemicals freely flow out; the first conductive portions 65A and 65B provided so as to be exposed in respective inner portions and respective outer portions of the bottle bodies 51A and 51B; and the second conductive portions 66A and 66B that are provided at respective positions different from those of the first conductive portions 65A and 65B so as to be exposed in the respective inner portions and the respective outer portion of the bottle bodies 51A and 51B, the second conductive portions 66A and 66B being electrically connected to the first conductive portions 65A and 65B via the respective chemicals in the bottle bodies 51A and 51B. Thus, the respective chemicals in the disinfecting chemical bottles 50A and 50B can directly be detected, and thus, a reliable agitation effect can be expected as a result of a diluting liquid being supplied along with outflow of the respective chemicals from the disinfecting chemical bottles 50A and 50B, enabling quick and accurate preparation of a disinfecting liquid with a uniform concentration. Furthermore, since a diluting liquid is supplied concurrently with outflow of the respective chemicals from the disinfecting chemical bottles 50A and 50B, the diluting tank 42 can reliably be prevented from deteriorating as a result of only the chemicals flowing into the diluting tank 42. In this case, as described in the present embodiment, at the time of replacement of the disinfecting chemical bottles 50A and 50B, a diluting liquid is made to flow in ahead of chemicals, enabling more reliable prevention of deterioration of the diluting tank 42, and the time for replacement of the disinfecting chemical bottles 50A and 50B can also be used as the time for chemical blending, enabling efficient (quick) chemical blending.

Although the present embodiment has been described in terms of an example in which the present invention has been applied to disinfecting chemical bottles 50A and 50B in a disinfecting chemical diluting mechanism 7 of an endoscope cleaning/disinfecting apparatus 1 including, e.g., a cleaning/disinfecting bath 3, a cleaning chemical diluting mechanism 6, a disinfecting chemical diluting mechanism 7, a control section 8, control valves and conduits such as illustrated in FIG. 1, the endoscope cleaning/disinfecting apparatus 1 may have another configuration. It should be understood that the present invention can be applied also to, for example, an apparatus including one disinfecting chemical bottle in a disinfecting chemical diluting mechanism 7 and a small-size apparatus in which disinfecting chemical bottle(s) are directly connected to a cleaning/disinfecting bath.

Also, although the embodiment of the present invention has been described in terms of an example in which the present invention has been applied to the disinfecting chemical bottles 50A and 50B in the disinfecting chemical diluting mechanism 7, the present invention can be applied also to the cleaning chemical bottle 29 in the cleaning chemical diluting mechanism 6, and the application of the present invention to the cleaning chemical bottle 29 enables quick and accurate preparation of a cleaning liquid with a uniform concentration without deterioration of a cleaning chemical diluting tank, enabling expansion of a range of choices for a cleaning chemical to be used.

Furthermore, an angle of inclination of the disinfecting chemical bottles 50A and 50B when the disinfecting chemical bottles 50A and 50B are attached to the bottle attachment portions 43A and 43B may be an arbitrary angle, and the present invention can be applied to, for example, even a case where the disinfecting chemical bottles 50A and 50B are suspended.

Also, the present invention is not limited to the respective embodiments described above, and various modifications, alterations and the like are possible without departing from the spirit of the present invention.

What is claimed is:

1. A chemical bottle for an endoscope cleaning/disinfecting apparatus, the chemical bottle comprising:
    a bottle body that is detachable from the endoscope cleaning/disinfecting apparatus, and includes a storing section that stores a chemical used for cleaning/disinfecting an endoscope, an opening portion that is provided at the storing section and from which the chemical freely flows out, and a cylindrical mouth portion surrounding the opening portion;
    a film portion provided between the storing section and the mouth portion, the film sealing the storing section;
    a first conductive portion made of an electrically conductive material and disposed through the storing section; and
    a second conductive portion made of an electrically conductive material and disposed through the mouth portion, wherein the first conductive portion and the second conductive portion are electrically connected to conduct electricity via the chemical when the film portion is broken and the chemical flows from the storing section to the mouth portion, wherein the first conductive portion and the second conductive portion are arranged, with the film portion interposed therebetween.

2. The chemical bottle for an endoscope cleaning/disinfecting apparatus according to claim 1, wherein the storing section comprises a first surface, a second surface facing the first surface, and a third surface connecting the first surface and the second surface, and
    wherein the opening portion is formed in the third surface at a position decentered toward the first surface, a part of the mouth portion is arranged on an extension of the first surface, the first conductive portion is formed in the first surface, and the second conductive portion is formed in the mouth portion on the extension of the first surface.

3. An endoscope cleaning/disinfecting apparatus comprising:
    the chemical bottle for an endoscope cleaning/disinfecting apparatus according to claim 1;
    a bottle disposition portion in which the chemical bottle for an endoscope cleaning/disinfecting apparatus inserted from outside of the bottle disposition portion is disposed, and the disposed chemical bottle is advanced to a predetermined position;

a first contact terminal formed in the bottle disposition portion and positioned so as to be in contact with the first conductive portion of the chemical bottle for an endoscope cleaning/disinfecting apparatus disposed at the bottle disposition portion;

a second contact terminal formed in the bottle disposition portion and positioned so as to be in contact with the second conductive portion of the chemical bottle for an endoscope cleaning/disinfecting apparatus disposed at the bottle disposition portion;

a protrusion portion positioned to come in contact with and break the film portion of the chemical bottle when the chemical bottle is advanced;

an electrical connection recognition section for recognizing an electrical connection between the first contact terminal and the second contact terminal by connecting the electrical connection recognition section to the first contact terminal and the second contact terminal; and an endoscope cleaning/disinfecting section connected to the bottle disposition portion.

4. The endoscope cleaning/disinfecting apparatus according to claim 3, wherein the storing section comprises a first surface to be positioned at a bottom when the chemical bottle is disposed in the bottle disposition portion, a second surface facing the first surface, and a third surface that connects the first surface and the second surface and faces the protrusion portion when the chemical bottle is disposed in the bottle disposition portion, and wherein the opening portion is formed in the third surface at a position decentered toward the first surface, a part of the mouth portion is arranged on an extension of the first surface, the first conductive portion is formed in the first surface, and the second conductive portion is formed in the mouth portion on the extension of the first surface.

\* \* \* \* \*